(12) United States Patent
Siegal et al.

(10) Patent No.: US 8,246,622 B2
(45) Date of Patent: Aug. 21, 2012

(54) TOOL AND CORRESPONDING METHOD FOR REMOVAL OF MATERIAL FROM WITHIN A BODY

(75) Inventors: Tzony Siegal, Moshav Shoeva (IL); Yinnon Elisha, Kfar Hees (IL); Dvir Keren, Tel Aviv (IL)

(73) Assignee: NLT-Spine Ltd., Kfar Saba (IL)

( * ) Notice: Subject to any disclaimer, the term of this patent is extended or adjusted under 35 U.S.C. 154(b) by 382 days.

(21) Appl. No.: 12/526,060

(22) PCT Filed: Jul. 27, 2009

(86) PCT No.: PCT/IB2009/053259
§ 371 (c)(1),
(2), (4) Date: Aug. 6, 2009

(87) PCT Pub. No.: WO2010/013188
PCT Pub. Date: Feb. 4, 2010

(65) Prior Publication Data
US 2010/0262147 A1  Oct. 14, 2010

Related U.S. Application Data

(60) Provisional application No. 61/083,931, filed on Jul. 27, 2008.

(51) Int. Cl.
*A61B 17/00* (2006.01)

(52) U.S. Cl. ........... 606/80; 606/79; 606/84; 606/85; 606/86 A

(58) Field of Classification Search ............ 606/79, 606/80, 83, 105
See application file for complete search history.

(56) References Cited

U.S. PATENT DOCUMENTS

| | | | |
|---|---|---|---|
| 5,285,795 A | 2/1994 | Ryan | |
| 6,641,582 B1 | 11/2003 | Hanson | |
| 7,578,820 B2 | 8/2009 | Moore | |
| 7,666,186 B2 | 2/2010 | Harp | |
| 7,837,687 B2 | 11/2010 | Harp | |
| 7,935,124 B2 | 5/2011 | Frey | |
| 8,062,298 B2 * | 11/2011 | Schmitz et al. | 606/79 |
| 2006/0036273 A1 * | 2/2006 | Siegal | 606/190 |
| 2007/0123986 A1 * | 5/2007 | Schaller | 623/17.11 |
| 2008/0103504 A1 | 5/2008 | Schmitz | |
| 2008/0243126 A1 | 10/2008 | Gutierrez | |
| 2010/0100098 A1 | 4/2010 | Norton | |
| 2010/0161060 A1 | 6/2010 | Schaller | |
| 2010/0217269 A1 | 8/2010 | Landes | |
| 2011/0009969 A1 | 1/2011 | Puno | |

* cited by examiner

*Primary Examiner* — Andrew Yang
(74) *Attorney, Agent, or Firm* — Mark M Friedman

(57) ABSTRACT

A device for removing material from within the body, includes an elongated element formed from hollow segments sequentially interconnected at effective hinges. The device assumes an insertion configuration for insertion of the segments sequentially through an opening of a first dimension into the body. A portion of the elongated element inserted into the body progressively assumes a material removing configuration in which a relative position of each segment relative to an adjacent segment is delineated by the effective hinge together with additional abutment surfaces defining a fully deflected state of the effective hinge. The material removing configuration has at least two dimensions exceeding the first dimension. At least two of the segments are formed with at least one cutting configuration deployed so as to collect material into a hollow volume of the segment during progressive formation of the material removing configuration as the elongated element is advanced.

21 Claims, 13 Drawing Sheets

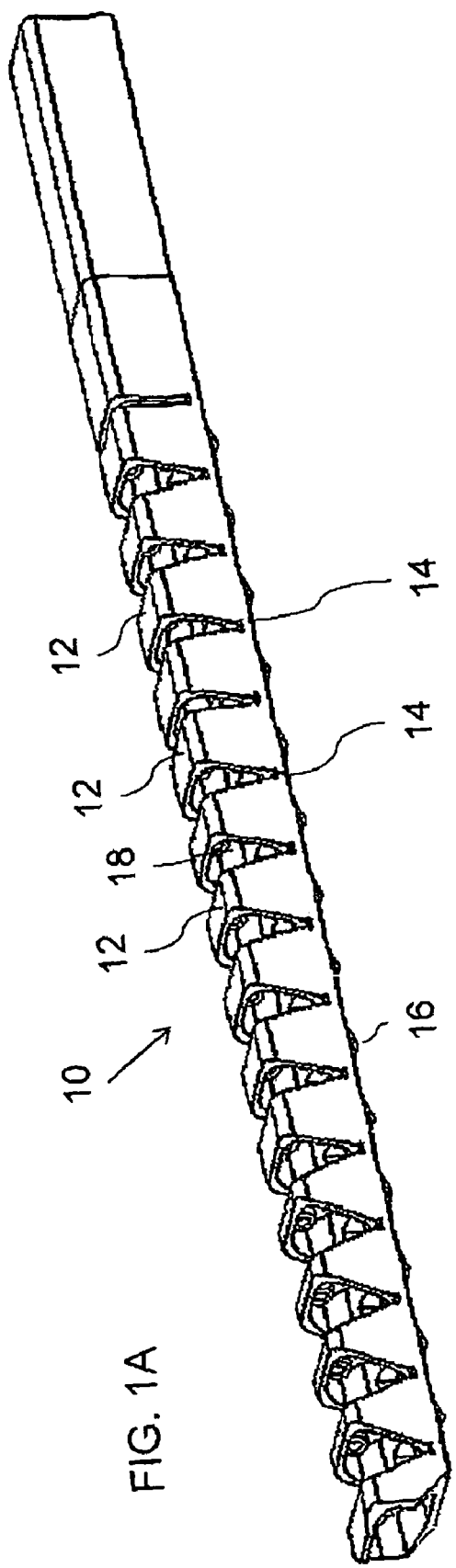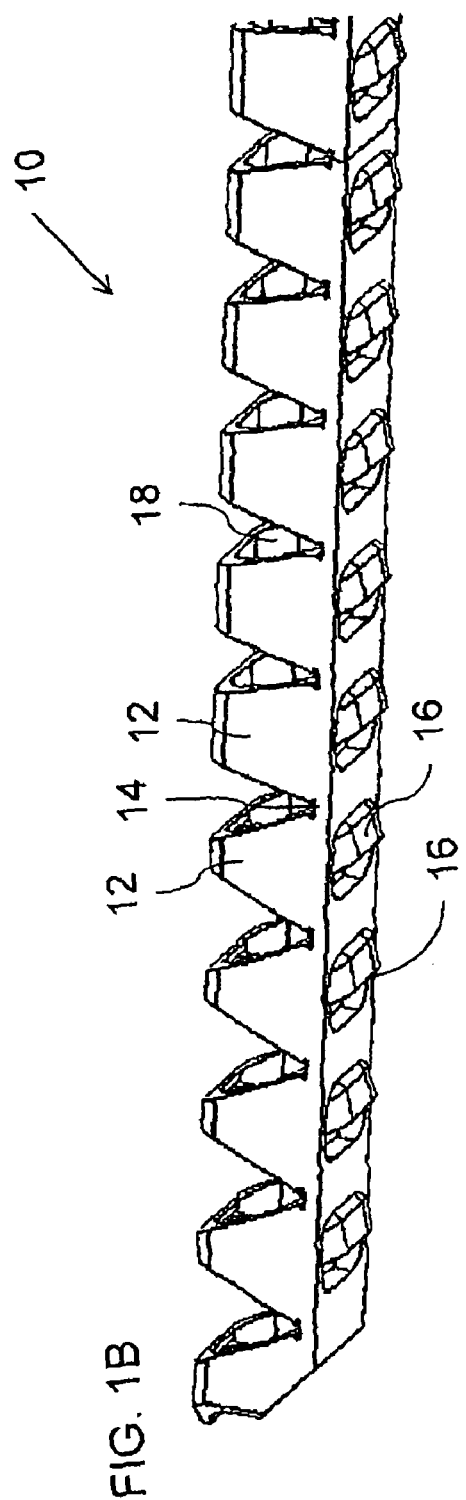
FIG. 1A
FIG. 1B

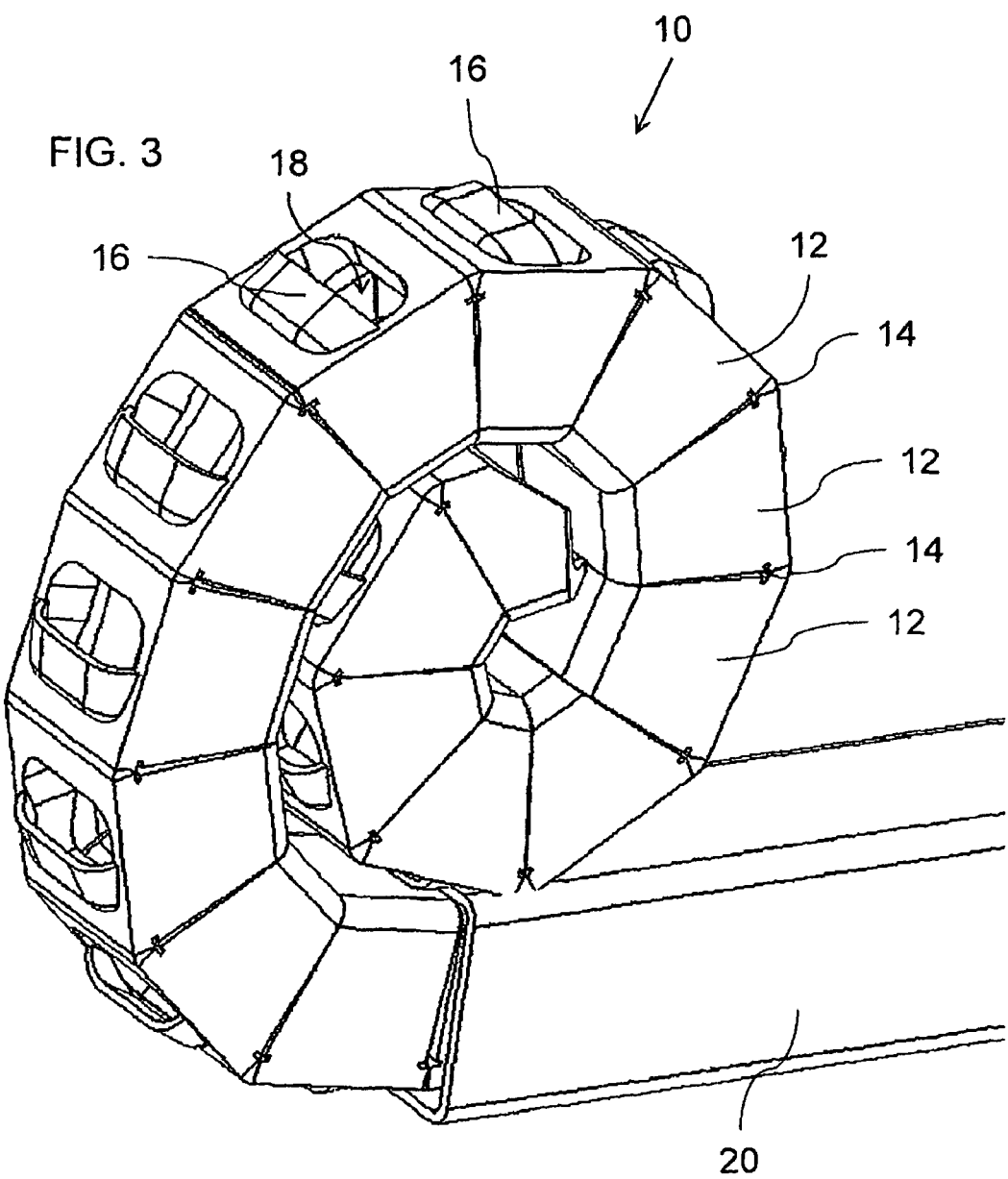

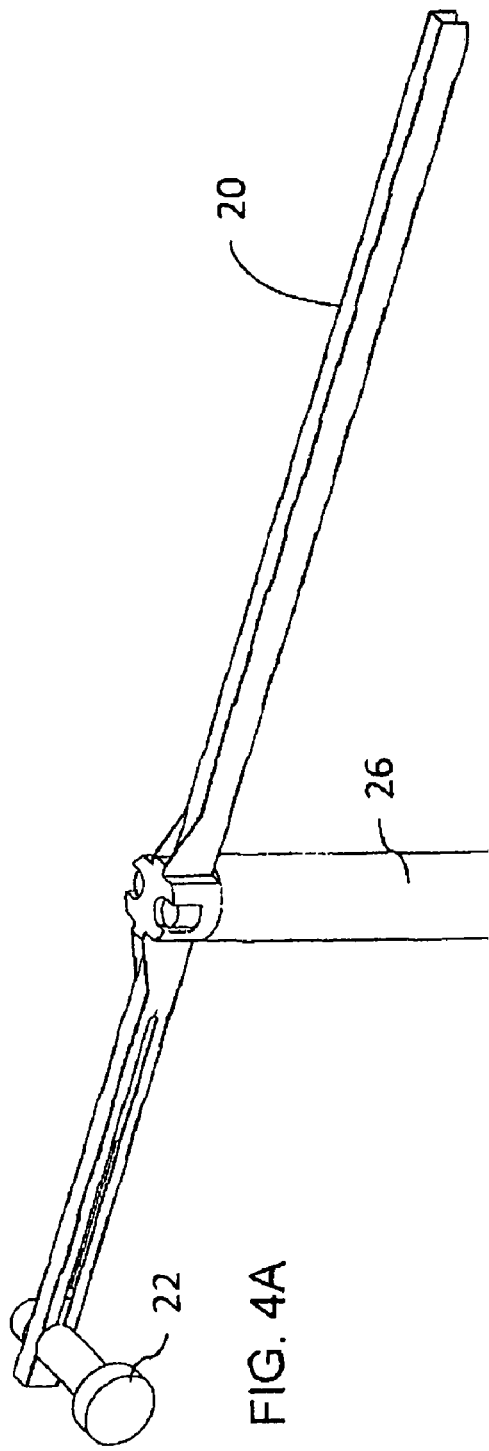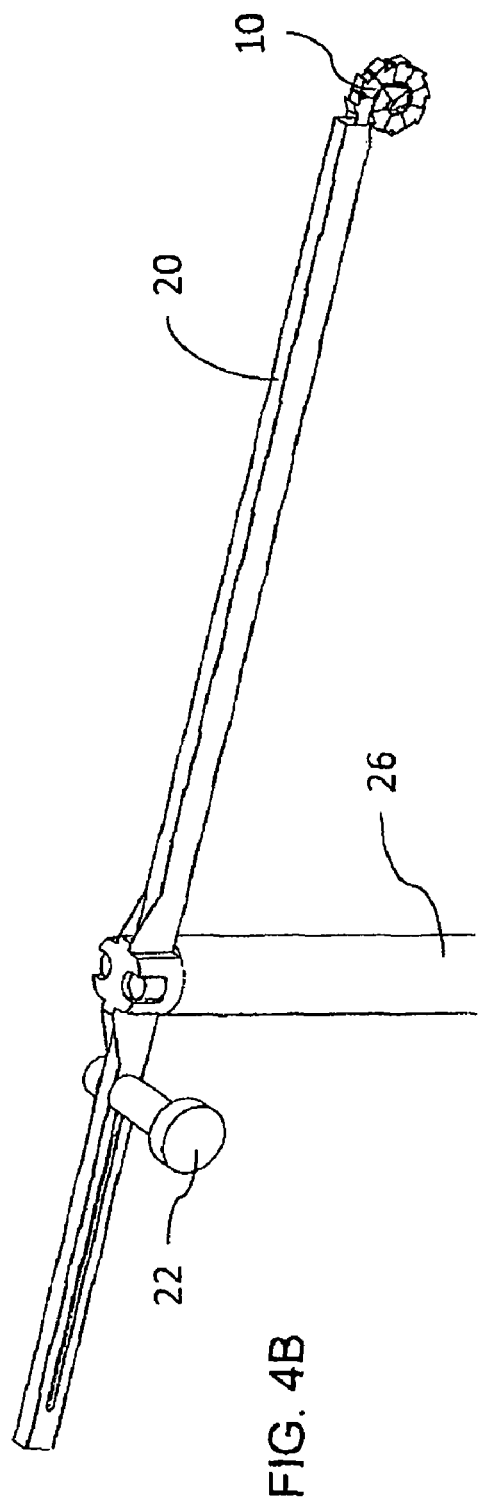

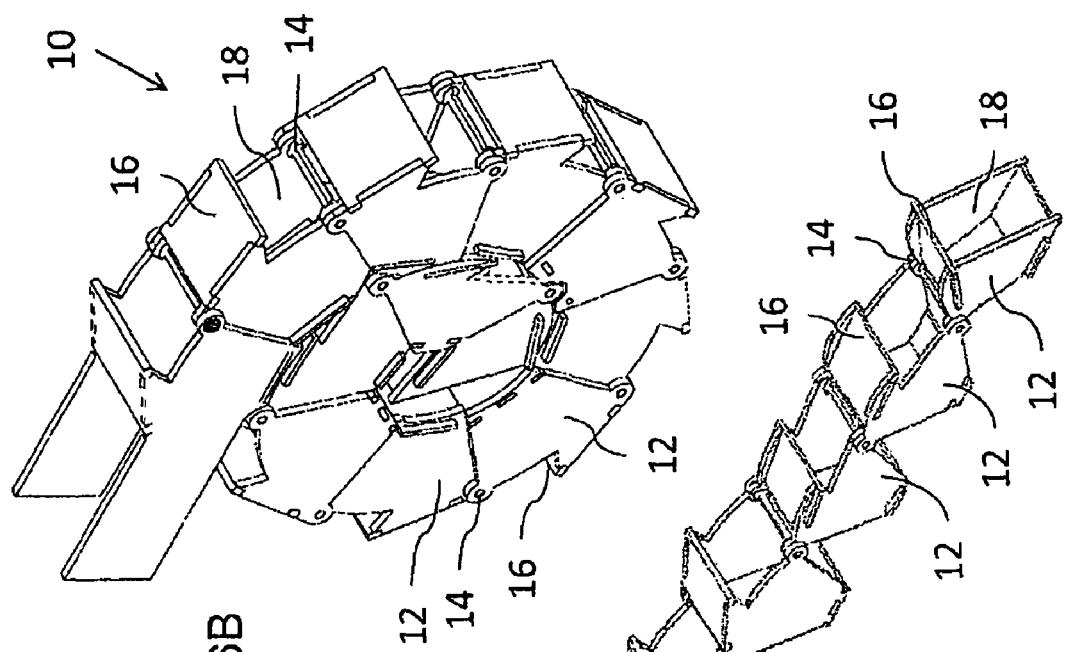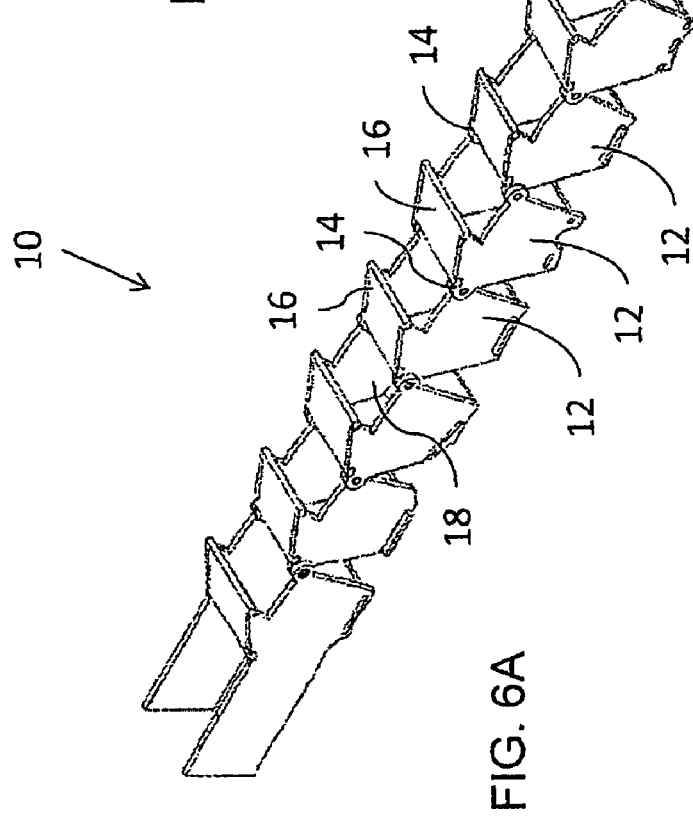

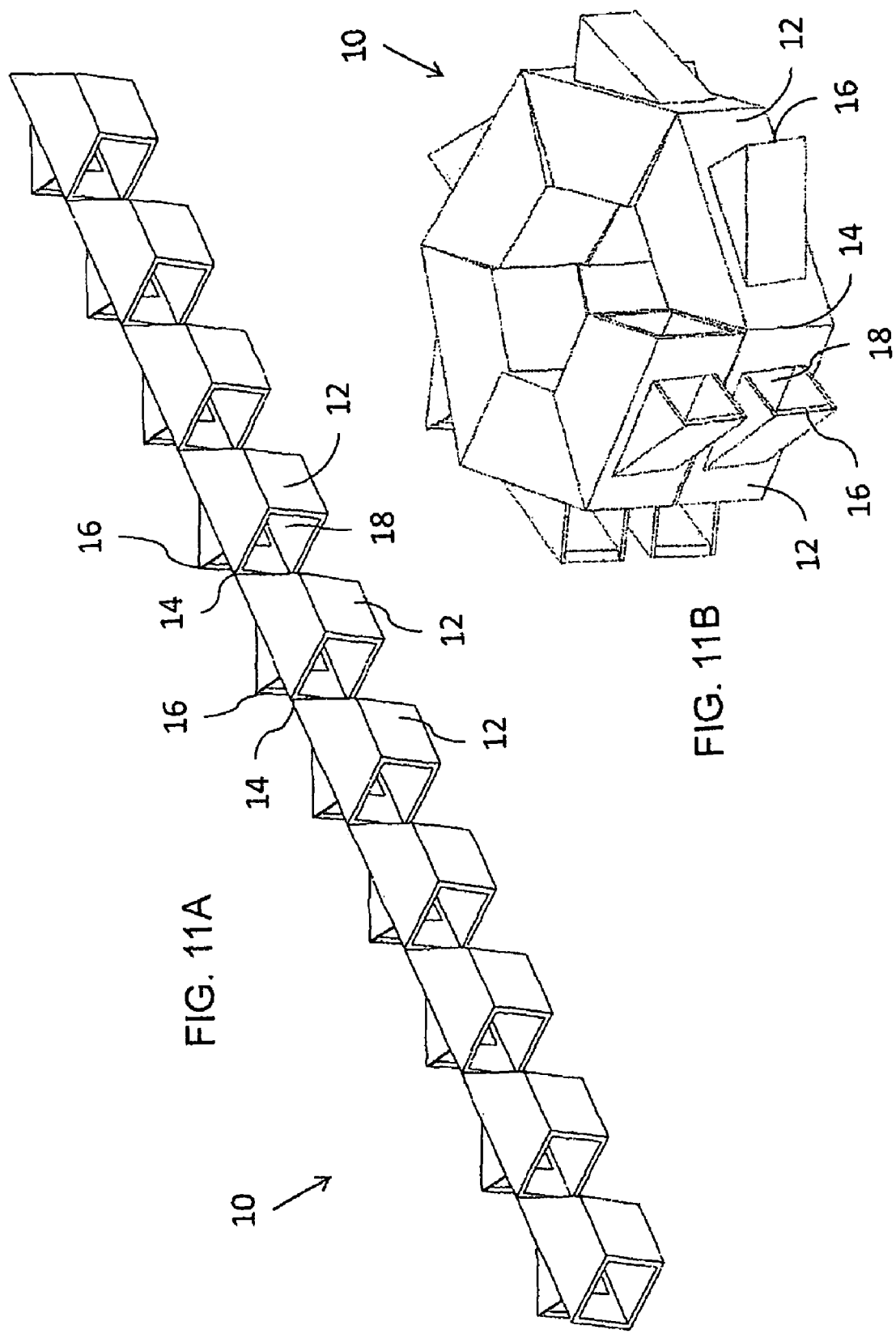

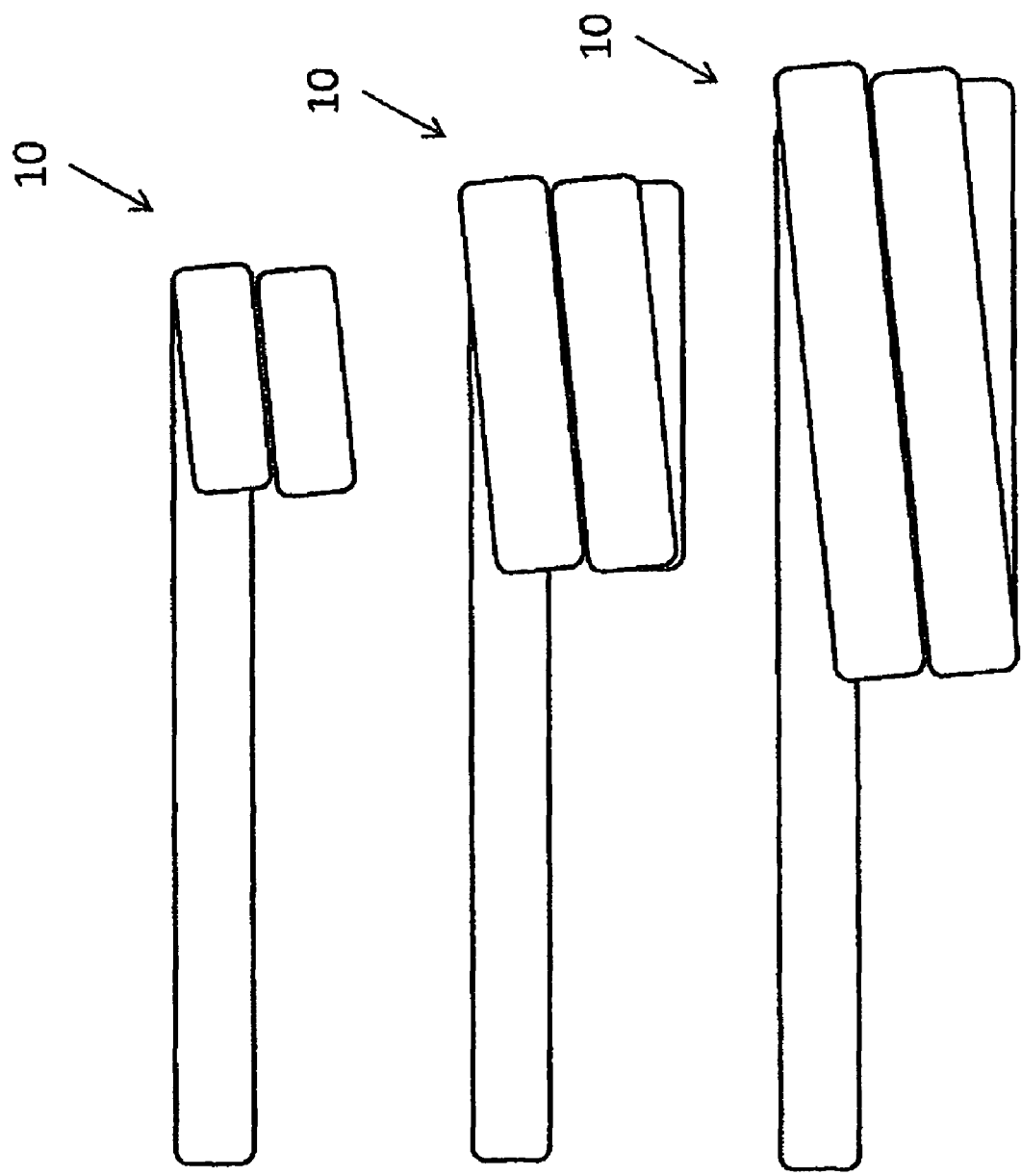

TOOL AND CORRESPONDING METHOD FOR REMOVAL OF MATERIAL FROM WITHIN A BODY

RELATED APPLICATIONS

This patent application is a National Stage of PCT/IB2009/053259 filed on Jul. 27, 2009, which claims the benefit under 119(e) of U.S. Provisional Patent Application No. 61/083,931 filed Jul. 27, 2008, the contents of which are incorporated herein by reference.

FIELD AND BACKGROUND OF THE INVENTION

The present invention relates to devices and methods for removing material from within a body, particularly where the volume of material to be removed has at least two dimensions exceeding the lateral dimensions of the opening via which the volume is accessed. In certain preferred embodiments, the invention provides a tool and method for removing material from an intervertebral disc, such as in a discectomy.

Various techniques are known for performing minimal-invasive discectomy. Most commonly, conventional cutting and manipulation tools are used under endoscopic control to sever disc tissue and remove it through a working channel. This approach is slow and tedious, particularly given limitations on the size of incision, and the risk of damage to the dural sac or nerve roots.

US Patent Application Publication No. 2007/0149990 to Palmer et al. proposes a tissue removal apparatus in which an elongated hollow device is formed from shape-memory materials that is biased to a predefined coiled form. The device has lateral cutting openings into which tissue is meant to be drawn under the influence of suction. The device is not sufficiently rigid to define a predictable path, and is described as loosening, tearing or disrupting tissue within the nucleus of the disc during insertion.

The unpredictability of the path that will be followed by the Palmer device during insertion may lead to a risk of perforation and injury. Additionally, the suction-based approach appears impractical for effective removal of material along a long narrow device with openings spaced along its length. Finally, the Palmer tool does not provide any direct volumetric control of the quantity of material removed.

Turning now to PCT Patent Application Publication No. WO 2006/072941 (hereafter "the '941 application"), this teaches a wide range of devices and corresponding applications in which an elongated element is introduced into a body in a straightened configuration and then assumes a curved or coiled configuration within the body. The '941 application is hereby incorporated by reference herein in its entirety. Unless otherwise defined, terminology used herein is used in the same sense as defined in the '941 application.

Certain embodiments described in the '941 application are implemented as hollow elements with an open tip and may perform limited tunneling or other removal of material from within a body. However, they are limited in their capabilities for removal of material from a volume within a body having at least two dimensions exceeding the lateral dimensions of the opening via which the volume is accessed.

Of particular relevance as background to the present invention are the planar spiral implementation of FIGS. 11-12C, and the three-dimensional forms of FIGS. 10, 13 and 14, of the '941 application. As defined there, and as used herein, the term "spiral" is used in its colloquial sense to refer to any shape which spirals inwards/outwards, and is not limited to an exact geometric spiral which is referred to herein as a "perfect spiral". The spiral formed from a stepped increase in radius of curvature as described here may be preferred due to its simplicity of manufacture. Nevertheless, it will be appreciated that it is possible to vary segment size and/or inter-segment spacing in a continuous manner to achieve a close approximation to a perfect spiral, or any other varying curvature profile desired.

There is therefore a need for a device for insertion into a body via an opening, and for removing material from within the body, which would follow a predefined path and provide controllable volumetric removal of material from a target region within the body.

SUMMARY OF THE INVENTION

The present invention is a device for insertion into a body via an opening, and for removing material from within the body.

According to the teachings of the present invention there is provided, a device for insertion into a body via an opening, and for removing material from within the body, the device comprising an elongated element formed primarily from a plurality of hollow segments sequentially interconnected so as to form an effective hinge between adjacent of the segments, the segments and the effective hinges being configured such that: (a) the elongated element assumes an insertion configuration for insertion of the segments sequentially through an opening of a first dimension into the body; and (b) a portion of the elongated element inserted into the body progressively assumes a material removing configuration in which a relative position of each segment relative to an adjacent segment is delineated by the effective hinge together with additional abutment surfaces defining a fully deflected state of the effective hinge, the material removing configuration having at least two dimensions exceeding the first dimension, wherein each of at least two of the segments is formed with at least one cutting configuration deployed so as to collect material into a hollow volume of the segment during progressive formation of the material removing configuration as the elongated element is advanced.

According to a further feature of the present invention, the elongated element is substantially straightened when in the insertion configuration.

According to a further feature of the present invention, the elongated element is resiliently biased to assume the material removing configuration.

According to a further feature of the present invention, the material removing configuration is configured such that, as the elongated element is advanced, the material removing configuration progressively expands in at least two dimensions.

According to a further feature of the present invention, the material removing configuration is configured to substantially close on itself so as to define a substantially contiguous contained volume.

According to a further feature of the present invention, at least part of the elongated element assumes a spiral configuration in the material removing configuration.

According to a further feature of the present invention, at least part of the elongated element assumes a helical configuration in the material removing configuration.

According to a further feature of the present invention, at least part of the elongated element assumes a conical shape in the material removing configuration.

According to a further feature of the present invention, the material removing configuration has three dimensions which all exceed the first dimension.

According to a further feature of the present invention, each of the segments has a substantially rectangular cross-section.

According to a further feature of the present invention, the at least one cutting configuration comprises at least one louver.

According to a further feature of the present invention, the at least one cutting configuration comprises at least two cutting configurations deployed on at least two sides of one of the segments.

According to a further feature of the present invention, the at least one cutting configuration comprises at least three cutting configurations deployed on at least three sides of one of the segments.

According to a further feature of the present invention, the elongated element includes at least five of the hollow segments.

There is also provided according to the teachings of the present invention, a method for removing material from a body, the method comprising: (a) providing a device comprising an elongated element formed primarily from a plurality of hollow segments sequentially interconnected so as to form an effective hinge between adjacent of the segments, the segments and the effective hinges being configured such that: (i) the elongated element assumes an insertion configuration for insertion of the segments sequentially through an opening of a first dimension into the body; and (ii) a portion of the elongated element inserted into the body progressively assumes a material removing configuration in which a relative position of each segment relative to an adjacent segment is delineated by the effective hinge together with additional abutment surfaces defining a fully deflected state of the effective hinge, the material removing configuration having at least two dimensions exceeding the first dimension, wherein each of at least two of the segments is formed with at least one cutting configuration deployed so as to collect material into a hollow volume of the segment during progressive formation of the material removing configuration as the elongated element is advanced; (b) deploying the device in a delivery system; (c) forming an opening into the body; (d) advancing the device through the opening into the body such that the device assumes the material removing configuration within the body; and (e) removing the device through the opening together with material collected within the hollow volume.

According to a further feature of the present invention, the material is at least part of an intervertebral disc.

According to a further feature of the present invention, the material is soft tissue.

According to a further feature of the present invention, the material is hard tissue.

BRIEF DESCRIPTION OF THE DRAWINGS

The invention is herein described, by way of example only, with reference to the accompanying drawings, wherein:

FIG. 1A is an isometric view of a device, constructed and operative according to an embodiment of the present invention, for removing material from within a body, the device being shown in a substantially straightened state prior to deployment;

FIG. 1B is an additional isometric view of a part of the device of FIG. 1A;

FIG. 3 is an enlarged view of the fully deployed state of the device of FIG. 1A;

FIGS. 4A and 4B are isometric views of an embodiment of the invention prior to and after deployment, respectively;

FIGS. 6A and 6B are enlarged isometric views of a device from the embodiment of FIGS. 4A and 4B, shown prior to and after deployment, respectively;

FIGS. 11A and 11B are schematic isometric views of a device, constructed and operative according to a further embodiment of the present invention, for removing material from within a body, the device being shown in a substantially straightened state prior to deployment and a curved deployed state, respectively;

FIGS. 12A-12C illustrate schematically a sequence of devices according to FIG. 11B for use in a procedure according to a further aspect of the present invention.

DESCRIPTION OF THE PREFERRED EMBODIMENTS

The present invention is a device for insertion into a body via an opening, and for removing material from within the body, particularly where the volume of material to be removed has at least two dimensions exceeding the lateral dimensions of the opening via which the volume is accessed.

The principles and operation of devices and methods according to the present invention may be better understood with reference to the drawings and the accompanying description.

Figure 8B:
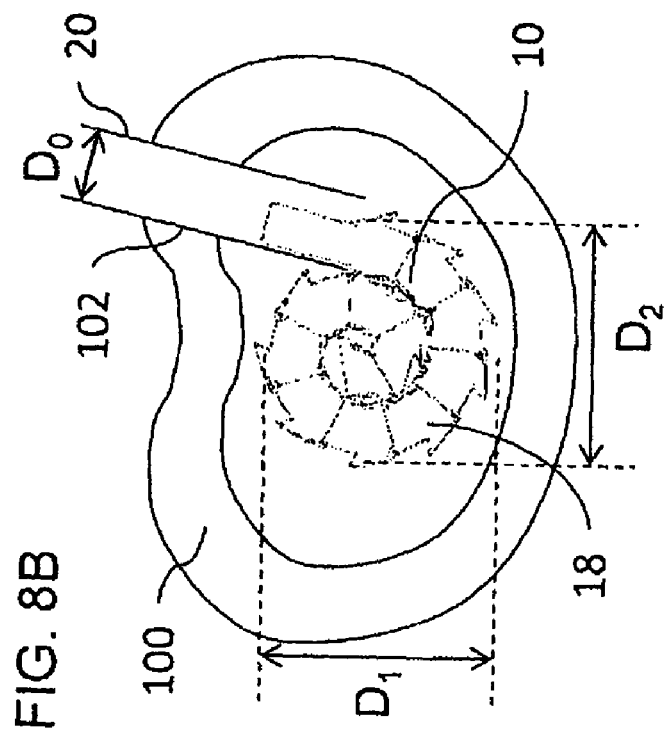
FIGS. 8A and 8B are schematic representations of two stages in a surgical procedure according to an aspect of the teachings of the present invention employing the embodiment of FIGS. 4A and 4B.
Figure 8A:
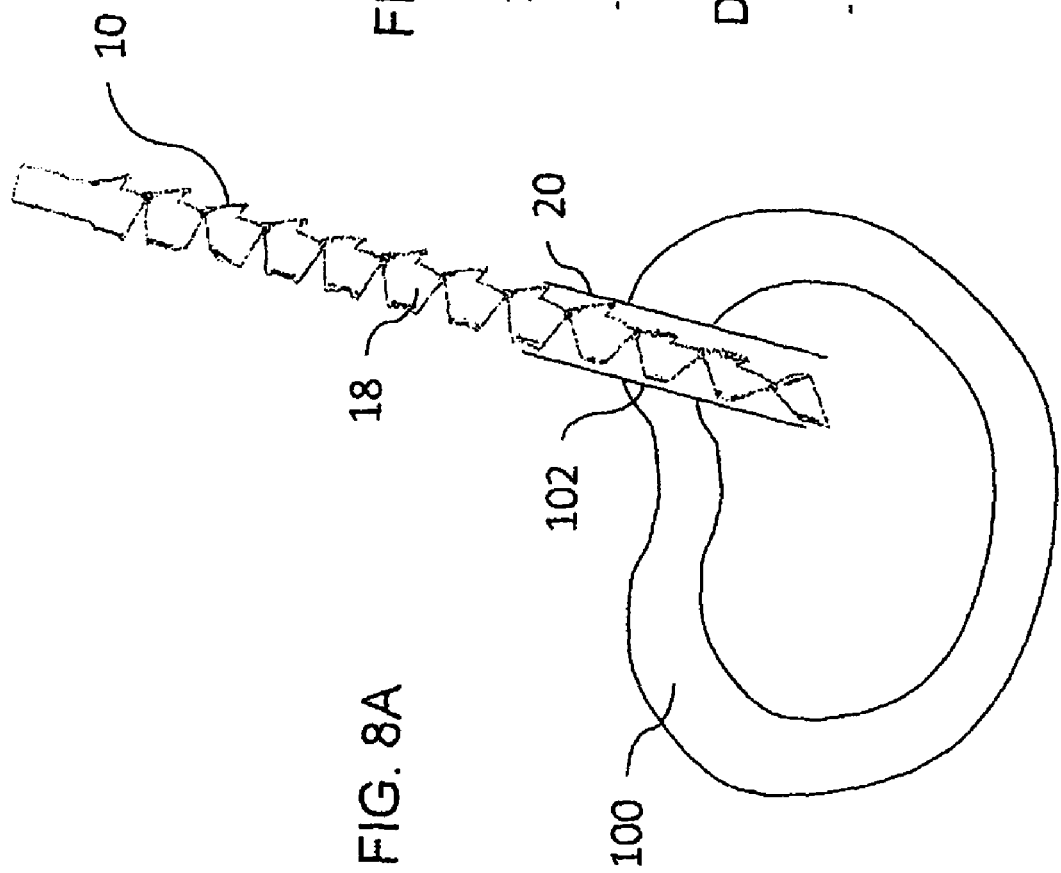

By way of introduction, and introducing reference numerals which will be used generically to refer to similar features throughout the drawings, certain embodiments of the present invention provide a device for insertion into a body via an opening, and for removing material from within the body. By way of one non-limiting example, FIGS. 8A and 8B show an intervertebral disc body 100 with an opening 102. For simplicity of presentation, in most of the drawings, the body and opening are omitted. Generally speaking, the device of certain embodiments includes an elongated element, generally designated 10, formed primarily from a plurality of hollow segments 12 sequentially interconnected so as to form an effective hinge 14 between adjacent segments. Segments 12 and effective hinges 14 are configured such that the elongated element assumes an insertion configuration, typically substantially straightened, for insertion of segments 12 sequentially through an opening of a first dimension $D_0$ into body 100, for example, as seen in FIG. 8A. Segments 12 and effective hinges 14 are further configured such that a portion of the elongated element inserted into the body progressively assumes a material removing configuration in which a relative position of each segment relative to an adjacent segment is delineated by the effective hinge together with additional abutment surfaces defining a fully deflected state of the effective hinge, for example, as shown in FIG. 8B. The material removing configuration preferably has at least two dimensions $D_1$ and $D_2$ exceeding first dimension $D_0$. It is a particular feature of an embodiment of the present invention that two or more of segments 12 are each formed with at least one cutting configuration 16 deployed so as to collect material into a hollow volume 18 of the segment during progressive formation of the material removing configuration as the elongated element is advanced.

The progressive deployment of various embodiments is best illustrated with reference to an embodiment of the invention illustrated in FIGS. 1A-3. Specifically, FIGS. 1A and 1B show an embodiment of a device, constructed and operative according to the teachings of the present invention, with elongated element 10 formed from a sequence of segments 12 interconnected at effective hinges 14 and exhibiting cutting configurations 16 deployed to collect material into a hollow volume 18. This embodiment may be regarded as an expanding cutter or "grater" formed from a spirally expanding element based on the principles of FIGS. 11-12C of the aforementioned '941 application. The cutting configuration may be any form of tooth, scoop or other cutting element configured and suitable implemented for collecting or cutting the particular material to be removed. In the preferred but non-limiting implementation illustrated here, cutting configuration 16 is a single wide scoop-like tooth. In the case of a metallic structure, this tooth may optionally be stamped out or otherwise formed in the metallic material from which the device is formed, resembling the "teeth" of a domestic grater. This structure is believed to be particularly suitable for removal of some, or substantially all, degenerated intervertebral disc material, in some cases in preparation for insertion of an intervertebral implant or graft, the size of which corresponds to the volume of disc removed.

In the exemplary embodiment shown here (FIGS. 1A-3), the grater is a hollow square tube which is incompletely cut at certain intervals, typically by removal of V-shaped slots of varying widths, rendering the tube as a series of links connected by integral joints. The angles between the links, defined by the width of the slots, are predesigned to allow curling of the structure in the same plane as the grater is propelled out of the delivering conduit. However, many other metals, alloys and non-metallic materials are also considered suitable.

Figure 2:
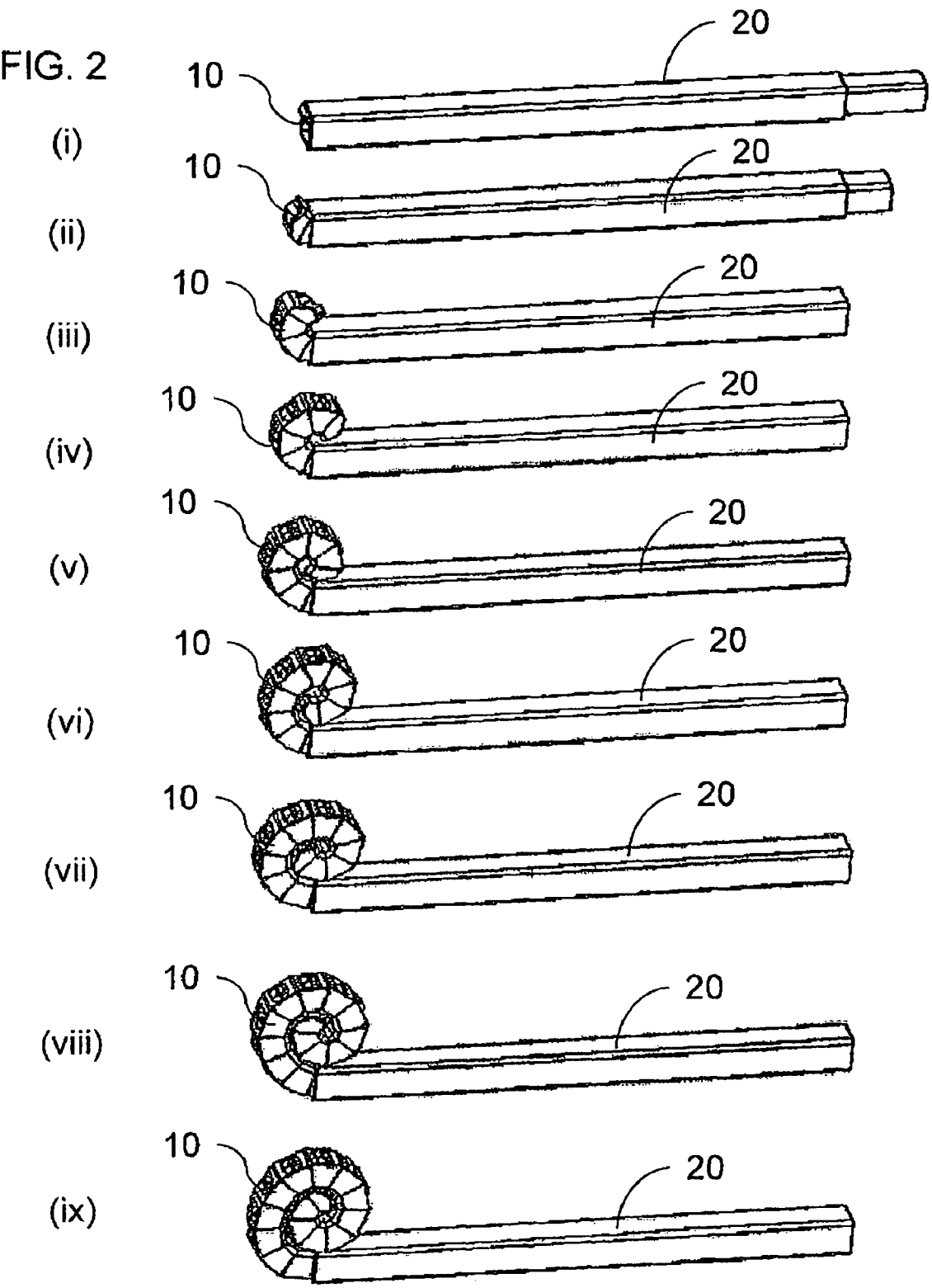
FIG. 2 is a sequence of views, labeled (i) through (ix), illustrating the progressive deployment of a material removal configuration according to embodiments of the present invention.

Operation of the device, corresponding to a method according to the present invention, may be understood by reference to the stages of deployment shown in FIG. 2. The device is brought to the desired location and is advanced beyond the end of a delivery conduit 20. The device curls on itself in gradually enlarging diameters, expanding in two dimensions and at the same time cutting/grating away the surrounding tissue (or other material) which is collected within the internal volume of the device. After the desired volume has been cut, the device is gradually withdrawn back into the conduit, and the conduit removed, taking with it the contained cut material. The hollow volume is then available for introduction of implants, etc.

The device of embodiments of the present invention is particularly applicable for deep tissue sampling, for removal of deep seated tissues (intervertebral discs, tumours etc.), and for creating voids or spaces to allow deployment of implants, introduction of bone cement, drug delivery, etc. in those spaces. The same underlying principles may be used to implement a device for industrial and other non-medical applications, for example, to create deep seated anchorage, obtained through small apertures.

The shape, size and positioning of the cutting configuration may be varied as needed. For example, in certain applications, the tooth may be wider, or a number of separate teeth may be deployed, to cut surrounding material from a width at least equal to the width of the body of segments of the instrument, thereby facilitating the radial expansion of the instrument even in relatively rigid material.

Optionally, the rearward-facing edge of the opening facing the cutting configuration may be implemented with a sharp edge and the internal lumen of the segments and/or the cutting configuration may be implemented with projecting retention features (not shown) to inhibit loss of the cut material during withdrawal of the cutting instrument. These retention features may include, but are not limited to, rearward-facing pins or barbs.

As mentioned earlier, the geometrical form of the cutting instrument in its deployed state need not be a perfect spiral, and may instead have groups of slots with the same width, or any other desired sequence of slot widths which define a gradually increasing diameter structure effective to achieve the desired expanding form.

Most preferably, a biasing arrangement is provided to bias the cutting instrument to its spirally curved deployed state as it emerges from the delivery conduit. This may simply be implemented as a tensioned element passing along the inside of the tool on the side facing inwards towards the center of the spiral. The element may be tensioned by a spring and/or an arrangement of gears, or by any other tensioning arrangement. Alternatively, shape memory properties may be employed to provide biasing to the deployed state. Examples of various biasing arrangements will be discussed further below. Additionally, or alternatively, an intersegment locking mechanism such as described in PCT Patent Application Publication No. WO 2008/084479 may be provided.

Turning now to an embodiment of the present invention illustrated with reference to FIGS. 4A-8B, this embodiment is generally similar to the embodiment of FIGS. 1A-3, also relating to a device which assumes a substantially spiral material-removing configuration. Throughout this document, except where explicitly contrasted, or where clearly incompatible, the various features of structure and operation of the various embodiments presented herein should be understood to be interchangeable between the embodiments. Thus, for example, the progressive deployment illustrated above with reference to FIG. 2 is equally applicable to all of the embodiments presented herein, while the delivery system and applications which will be described with reference to FIGS. 4A-8B are also equally applicable to all of the embodiments presented herein.

Figure 5A:
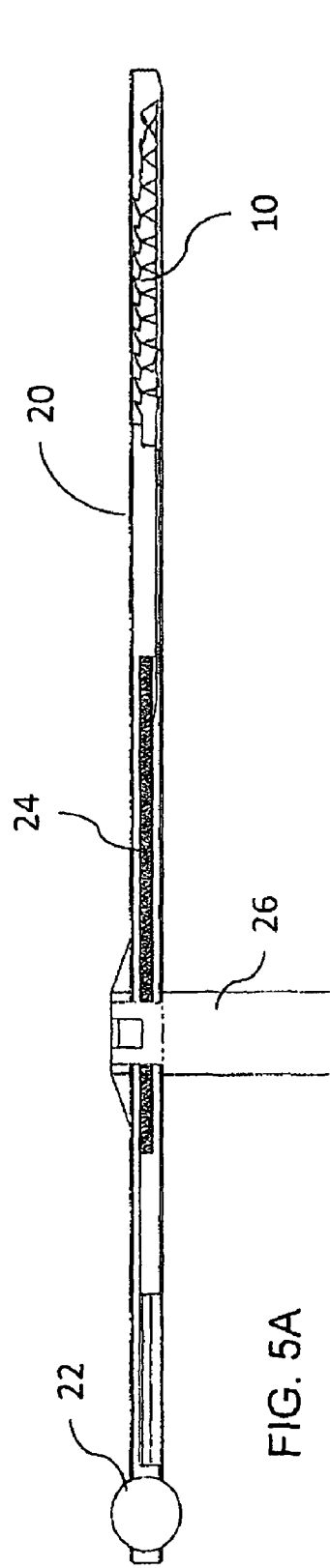
FIGS. 5A and 5B are isometric side views of the embodiment of FIGS. 4A and 4B with a side cover of a delivery system removed, prior to and after deployment, respectively.
Figure 5B:
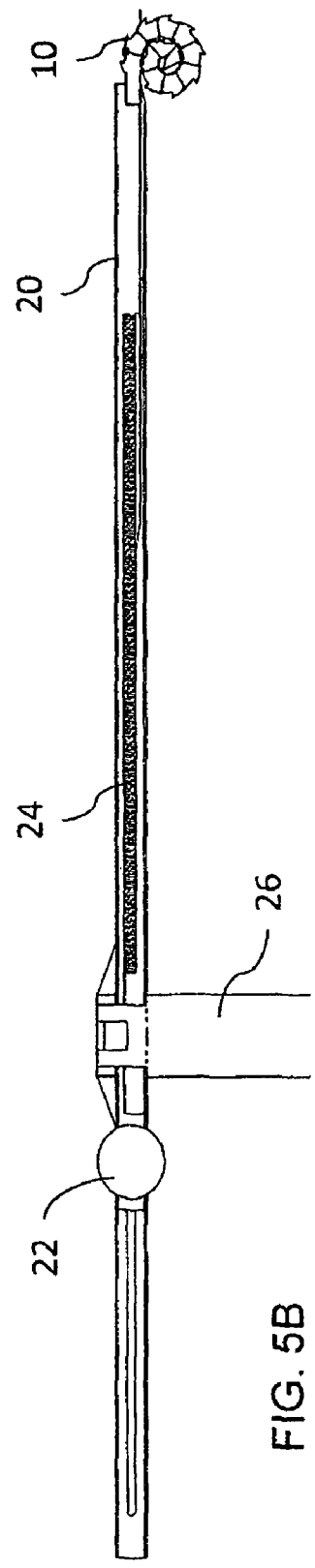

Referring specifically to FIGS. 4A-5B, these show an example of a delivery system for operating embodiments of the present invention. FIGS. 4A and 5A show conduit 20 with elongated element 10 withdrawn inside it in a substantially straightened state, either prior to deployment or after withdrawal, while FIGS. 4B and 5B show elongated element 10 in its fully deployed material-removing configuration. The example illustrated here is configured for manual operation, by rotating knob 22 which includes a gear wheel engaged on a gear tooth rack (not shown), thereby providing controllable and precise motion of the device along conduit 20. Clearly, alternative manual actuators, and various electrical or otherwise powered actuators, may readily be implemented by one ordinarily skilled in the art.

It will be noted that embodiments of the present invention provide volumetric material removal. Specifically, since the path followed by elongated element 10 during deployment is well defined, and the volume swept through by elongated element 10 at any stage of deployment is known, it is possible to define with considerable accuracy what volume of material will be removed by advancing the device to various defined positions. Thus, in an embodiment of the present invention, the delivery system provides graduated markings, or otherwise indicates quantitative information associated with the actuation mechanism, to allow an operator to remove a controlled and defined quantity of material from within the body.

As best seen in FIGS. 5A and 5B, this implementation of the delivery system also includes a biasing spring 24 deployed to maintain the aforementioned bias of elongated element 10 towards its closed material-removing configuration by applying tension to a tensioning element or "drawcord" (not shown) deployed along the elongated element. It will be understood that, during successive deployment of elongated element 10, relative motion occurs between the elongated element and the draw-cord. The resulting slack can either be taken up elastically by the spring, or can be compensated by implementing a differential gear arrangement which causes different rates of movement of the elongated element and the anchor of the spring. In alternative embodiments where the hinged interconnection or other local intersegment elements provide this bias, biasing spring 24 may be omitted.

The biasing arrangement is preferably configured to provide relatively strong biasing such that, under normal operating conditions, elongated element 10 at all stages assumes a well defined and substantially rigid form in which any portion of the element still within conduit 20 is maintained in its straightened state and any part already extending beyond the end of conduit 20 assumes its fully-deflected curved (e.g., spiral) state. As a result, elongated element 10 follows a well defined and predictable path as it advances into the body, thereby minimizing risks of damage such as may be caused by various types of flexible tools which may inadvertently stray from their planned paths. The rigidity of the device is further enhanced in certain embodiments where loops of the resulting structure close against each other in direct contact.

The deployment device also includes a support shaft 26 which may be clamped in a given position so as to support conduit 20 in a desired position and orientation. Optionally, an endoscope (not shown) can be incorporated with conduit 20 to facilitate inspection of the results of the material removal. Alternatively, after completion of a material-removal procedure, the device can be withdrawn from at least part of conduit 20 to allow insertion of a stand-alone endoscope along the conduit lumen for the same purpose.

Although illustrated here with a straight conduit 20, it will be clear that conduit 20 may be implemented with various degrees of curvature without adversely affecting operation of the invention, and in certain cases, to advantage. Even in cases where conduit 20 exhibits significant curvature, the state of elongated element 10 within the conduit is referred to as "substantially straightened", in clear contrast to the curved deployed state which the element assumes on leaving the conduit.

Figure 7A:
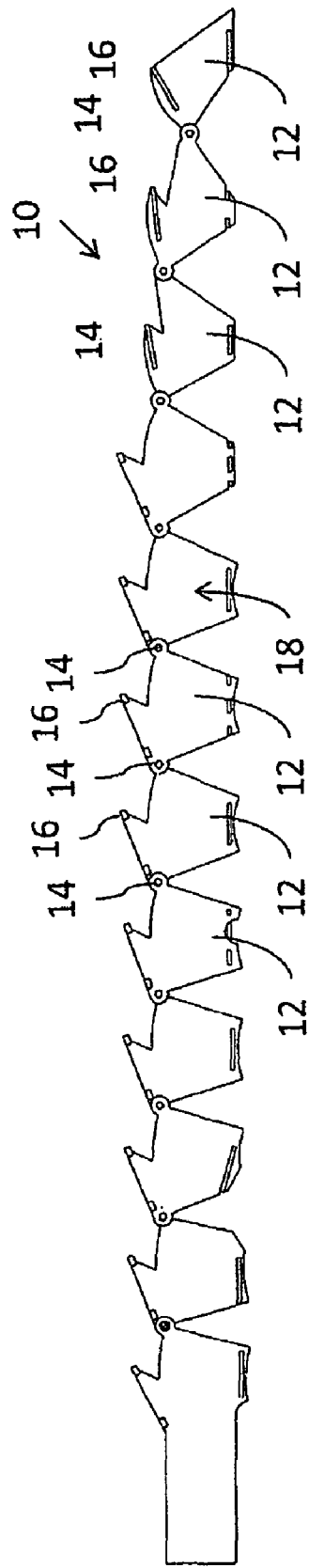
FIGS. 7A and 7B are enlarged side views of the device of FIGS. 6A and 6B.
Figure 7B:
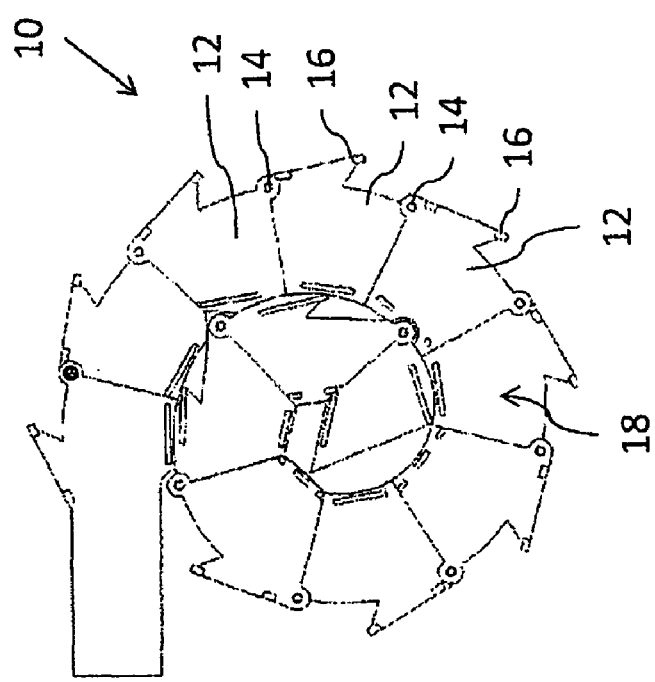

FIGS. 6A-7B show an embodiment of elongated element 10 in more detail, with FIGS. 6A and 7A showing the substantially straightened configuration and FIGS. 6B and 7B showing the fully deployed material-removing configuration. This embodiment differs from that of FIGS. 1A-3 in that it employs dedicated hinge structures to define effective hinges 14 with precise hinge axes between segments. This embodiment also employs individually varying segment shapes in order to substantially close on itself so as to define a substantially contiguous contained volume. In this context, "substantially contiguous" is used to refer to a deployed material-removing configuration in which spaces between successive turns of the structure are minimized. As a result, the device is typically effective to remove a block of material to leave a roughly unitary cavity within the body.

In the particular preferred embodiment illustrated here, the form of the segments and the position of the hinges is configured to achieve a close approximation to an Archimedean spiral. This form has the added advantages of employing segments of roughly uniform heights (radial steps in the spiral) and maintaining a roughly linear relation between the length of the elongated element deployed and the volume of material removed.

This embodiment is illustrated here with 11 hinged segments 12. The number of segments can clearly be varied according to the intended application, primarily as a function of the ratio of the volume to be removed and the dimensions of the opening through which access is achieved. Typically, elongated element 10 includes a minimum of five hinged segments 12, and preferably at least 10 hinged segments. Preferably, no more than 30 segments are used.

The cutting configurations 16 in this embodiment are implemented as slats or "louvers" which extend across the full width of segments 12. Depending on the type of material to be removed and the design considerations of the device, these louvers may be either unsharpened wall portions or they may feature a sharpened cutting edge, with or without serrations or other cutting enhancing features. The cutting edges and/or entire cutting configurations may be implemented from the same materials used for the rest of segments 12 or may be implemented from different materials or with specific coatings to impart specific mechanical or physiological properties. For example, in certain non-limiting implementations, part or all of the cutting configurations are coated in a low-friction material, such as PTFE, so as to facilitate passage of material into contained volume 18. The inner lumen of the device may have a relatively higher friction surface which helps to grip the contained material while the device is removed.

It should be noted that the term "cutting configuration" is used herein to refer to any cutting configuration which enables a segment 12 other than the leading segment of elongated element 10 to cut material in contact with which it is moving. In this sense, they may be referred to as "lateral cutting configurations." In the case of the spiral expansion illustrated here, the primary cutting direction is in the radially outward direction as shown here.

Figure 9B:
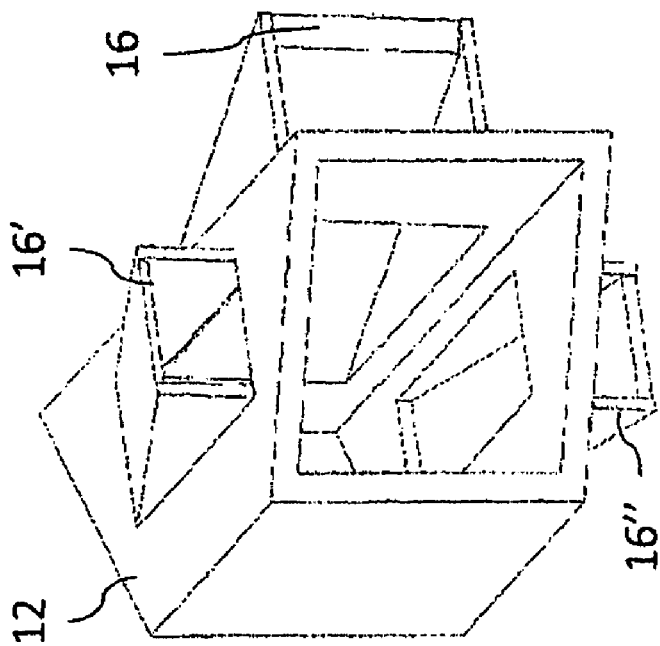
FIGS. 9A and 9B are schematic isometric views of alternative implementations of a segment of the device of FIGS. 6A and 6B.
Figure 9A:
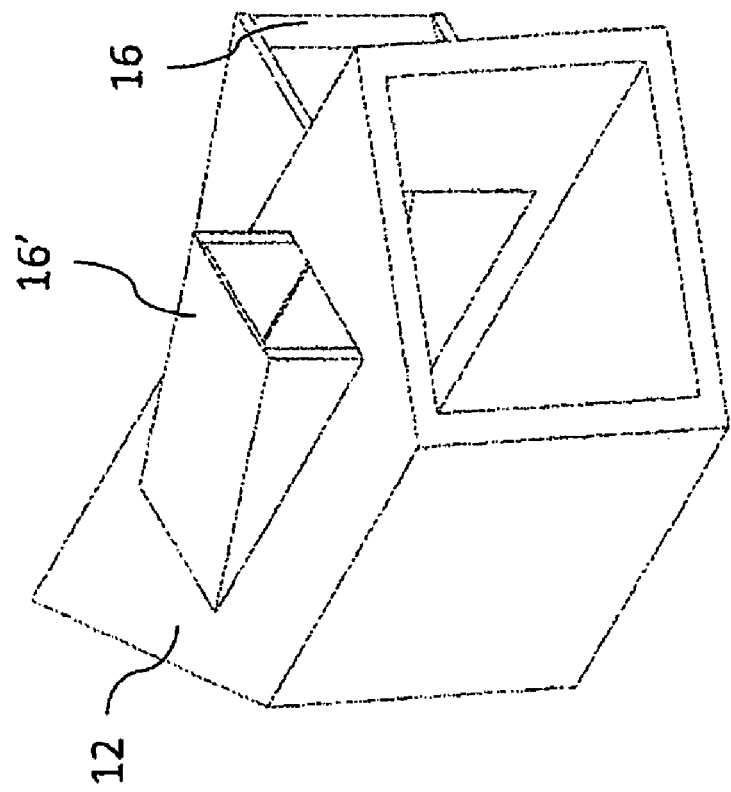

Referring parenthetically to FIGS. 9A and 9B, embodiments of the present invention are not limited to cutting in a single lateral direction. FIG. 9A illustrates an example in which some or all of segments 12 are implemented as shown with two cutting configurations 16 and 16' deployed on two sides of the segments. FIG. 9B illustrates an example in which some or all of segments 12 are implemented as shown with three cutting configurations 16, 16' and 16" deployed on three sides of the segment. These embodiments may be used to advantage in cases where the elongated element expands in three dimensions during deployment in the material-removing configuration, or even in a planar (e.g., spiral) embodiment where the device expands between inwardly pressing layers of tissue.

Referring again to FIG. 6A, the embodiment illustrated here employs segments which have alternating larger and smaller widths (i.e., the dimension parallel to the effective hinges). Optionally, this allows the edges of adjacent segments to be implemented with slight overlap in the deployed state. In certain preferred embodiments, the overlapping edges are configured to come together with a scissors cutting action which may provide an additional cutting effect. This effect may be particularly helpful where significant mechanical forces are encountered resisting advancing of the device, sometimes acting against the aforementioned biasing arrangements to cause momentary opening of gaps between the segments. The scissors cutting action is then effective to facilitate re-closure of the structure, and provides and added cutting effect.

Turning now to FIGS. 8A and 8B, an application of an embodiment of the invention for intervertebral discectomy is illustrated. The device is deployed with elongated element 10 within delivery conduit 20 of the delivery system (not shown), and the delivery conduit 20 is inserted through an opening 102 in the body 100 (FIG. 8A). The device is then advanced via conduit 20 through opening 102 into body 100 such that it assumes the material removing configuration within the body (FIG. 8B). The device is then removed via conduit 20 through opening 102 together with the material collected within the hollow volume.

As mentioned above, at least two dimensions $D_1$ and $D_2$ of the material removing configuration are preferably greater than the dimension $D_0$ of opening 102. In this context, the dimension $D_0$ may be taken as the largest dimension to which the minimally invasive incision is opened. For the purposes of evaluating a device according to the present invention, for practical purposes, dimension $D_0$ may be taken to be the maximum transverse dimension of the part of conduit 20 which is inserted into the body.

The procedure described with reference to FIGS. 8A and 8B may be employed as a step in a wide range of surgical procedures. In a simple example, the process may be a self-contained process for removal of tissue, for example, for reduction of intra-discal pressure to alleviate a herniated disc and/or for a biopsy. In the case of a biopsy, a complementary tool, typically in the form of a rectangular rod, may be provided for insertion along elongated element 10 after use, typically from the distal tip in a proximal direction, to expel the sampled material from contained volume 18 when required.

Alternatively, removal of material from an intervertebral disc may be performed to clear space for introduction of a spacer or other mobility-preserving implant, or for delivery of various drugs, brachytherapy seeds or other materials or tools.

In cases of vertebral fusion, the procedure may be performed once or more until bleeding bone is exposed for the two facing vertebral surfaces, followed by introduction of a cage and/or introduction of filler material, cement, bone, bone graft material, bone morphogenetic proteins, osteogenetic material etc., for promoting fusion of the adjacent vertebral bodies.

Where a device or other materials are to be delivered to the intra-body site, this may advantageously be performed after removal of elongated element 10 via the same conduit 20 used for insertion of the device. In certain implementations of the invention, such devices or materials may be introduced along the lumen of another subsequently inserted elongated element 10 inserted after initial removal of material from within the body.

It will be clear that embodiments of the present invention allow removal of significant quantities of material from within a body in an efficient, reliable and predictable manner via a small incision. For example, continuing with the example of removal of material from an intervertebral disc, an exemplary device for insertion via an opening of transverse dimensions no more than 4.5 mm by 4.5 mm is preferably configured to remove a quantity in excess of 1 cc, and most preferably at least 2 cc. For this purpose, a device of length (when straightened) of at least about 15 cm, and preferably at least about 20 cm, is used.

Although illustrated here in a particularly preferred exemplary application of surgery involving an intravertebral disc, it should be appreciated that the invention is not limited to such applications, and may readily be used in a range of other applications. Additional non-limiting examples include procedures for performing biopsy of bone tissue, for example, in vertebral bodies or in a femur.

Figure 10B:
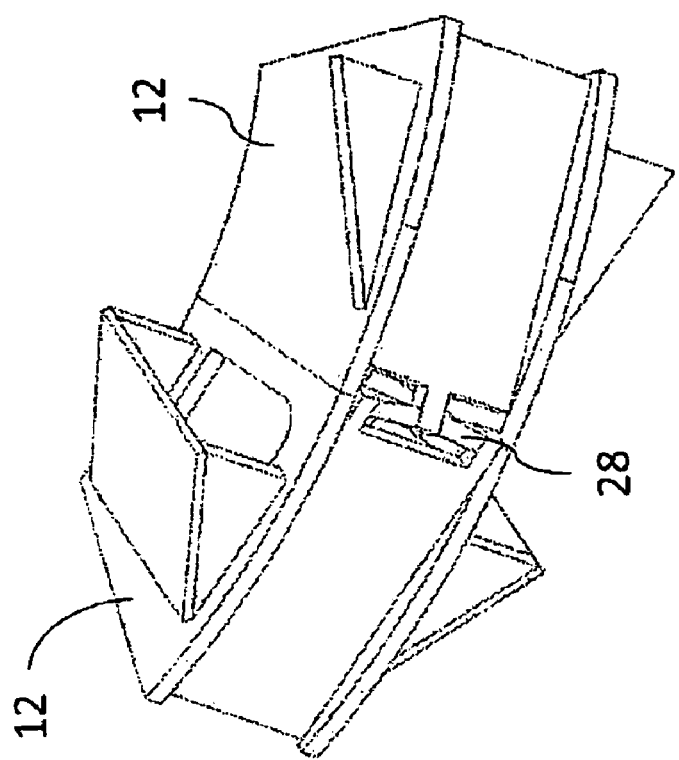
FIGS. 10A and 10B are schematic isometric views of an implementation of a hinged interconnection between two segments, shown in a substantially straightened and a closed, deflected state, respectively, according to a variant implementation of the device of FIGS. 6A and 6B.
Figure 10A:
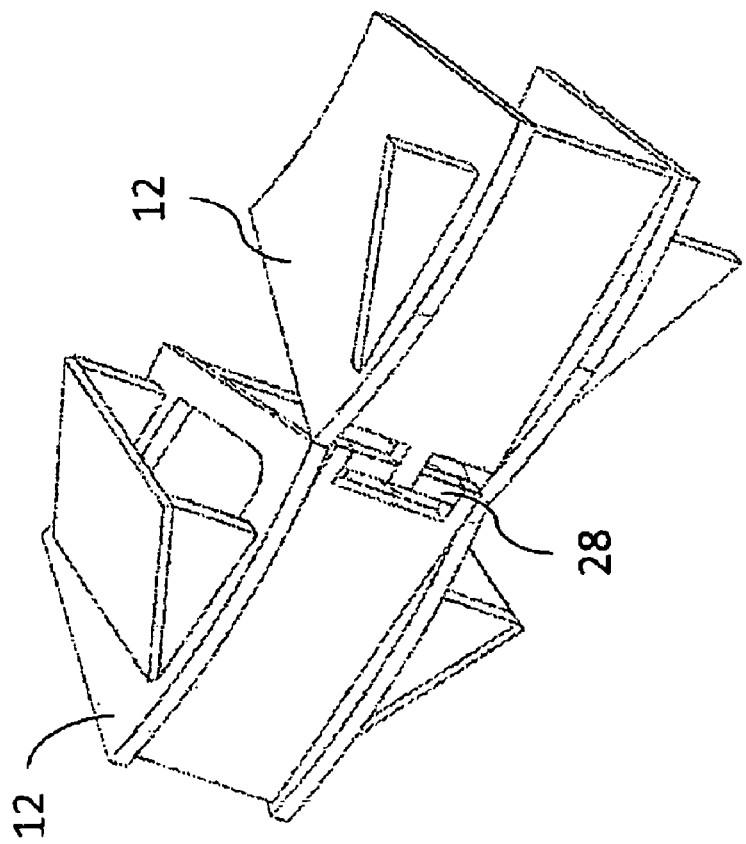

Turning now to FIGS. 10A and 10B, these drawings illustrate an alternative form of effective hinge attachment between adjacent segments 12, which may be implemented to particular advantage using shape-memory materials. In certain cases, an integral hinge may not provide a required level of precision as to the position of the axis of rotation. On the other hand, assembly of separate hinge structures may present manufacturing challenges, and typically does not allow for incorporating resilient biasing into the hinge structure itself. This embodiment presents an alternative form of effective hinge which can be manufactured as part of the segment structure but which also provides precise location of the hinge axis of rotation.

Specifically, the implementation shown here employs a torsion bar 28 to define the axis of rotation. The ends of torsion bar 28 are anchored to one segment while the middle of the bar is anchored to the adjacent segment. This allows effective hinge motion between the two segments between an open/straightened position as in FIG. 10A and a closed position as in FIG. 10B for forming the material-removing configuration.

In certain cases, the structure shown may advantageously be formed from a shape-memory material, such as Nitinol, preformed to return to the closed state of FIG. 10B. In this way, the hinge structure itself provides the aforementioned resilient bias for the device to assume its material-removing configuration.

Turning now to FIGS. 11A-12C, in contrast to the spiral configurations illustrated above, these drawings illustrate an embodiment of the invention in which elongated element 10 assumes a generally helical material-removing configuration. As described in the '941 application, deployment of the effective hinge axis at a slightly oblique angle generates a helical progression of the element in its closed state. Here too, this progression can be used to advantage with addition of lateral cutting configurations to achieve effective removal of material. This approach facilitates removal of a volume of material with three dimensions which all exceed the dimension of the opening through which the device is inserted. This is particularly advantageous in allowing delivery of a device of given dimensions via a minimally invasive incision of dimensions significantly smaller than would be required by other techniques, with resulting improvements in safety of the procedure and reduction in recovery times.

A helical implementation typically performs much of the material cutting with the open end of the leading segment, while the outward projecting lateral cutting configurations further contribute to increasing the diameter of the hollowed volume and smoothing or scraping the surfaces. Additionally, or alternatively, axially projecting lateral cutting configurations (not shown) may be deployed on the top loop of the helix in order to enhance the axial (height) progression of the device.

Embodiments such as the helical embodiment in which the leading segment remains in a leading position open up additional options of using the inner lumen of the device, prior to, during and/or after insertion as a passageway for deployment of additional tools and/or materials. According to one non-limiting example, an oversize drill bit or other device for breaking-up the material ahead of the device can be driven by a flexible drive shaft passing along the lumen, thereby facilitating advance of the device through the material.

In some cases, a helical removal structure leaves a central core of uncut material. If necessary, the central core which lies within the helical structure may be removed by conventional techniques after elongated element 10 has been withdrawn. Alternatively, as illustrated schematically in FIGS. 12A-12C, effective complete removal of any desired volume of material may be achieved by using a sequence of helical elements designed to form material-removing configurations of a sequence of different diameters.

Figure 13:
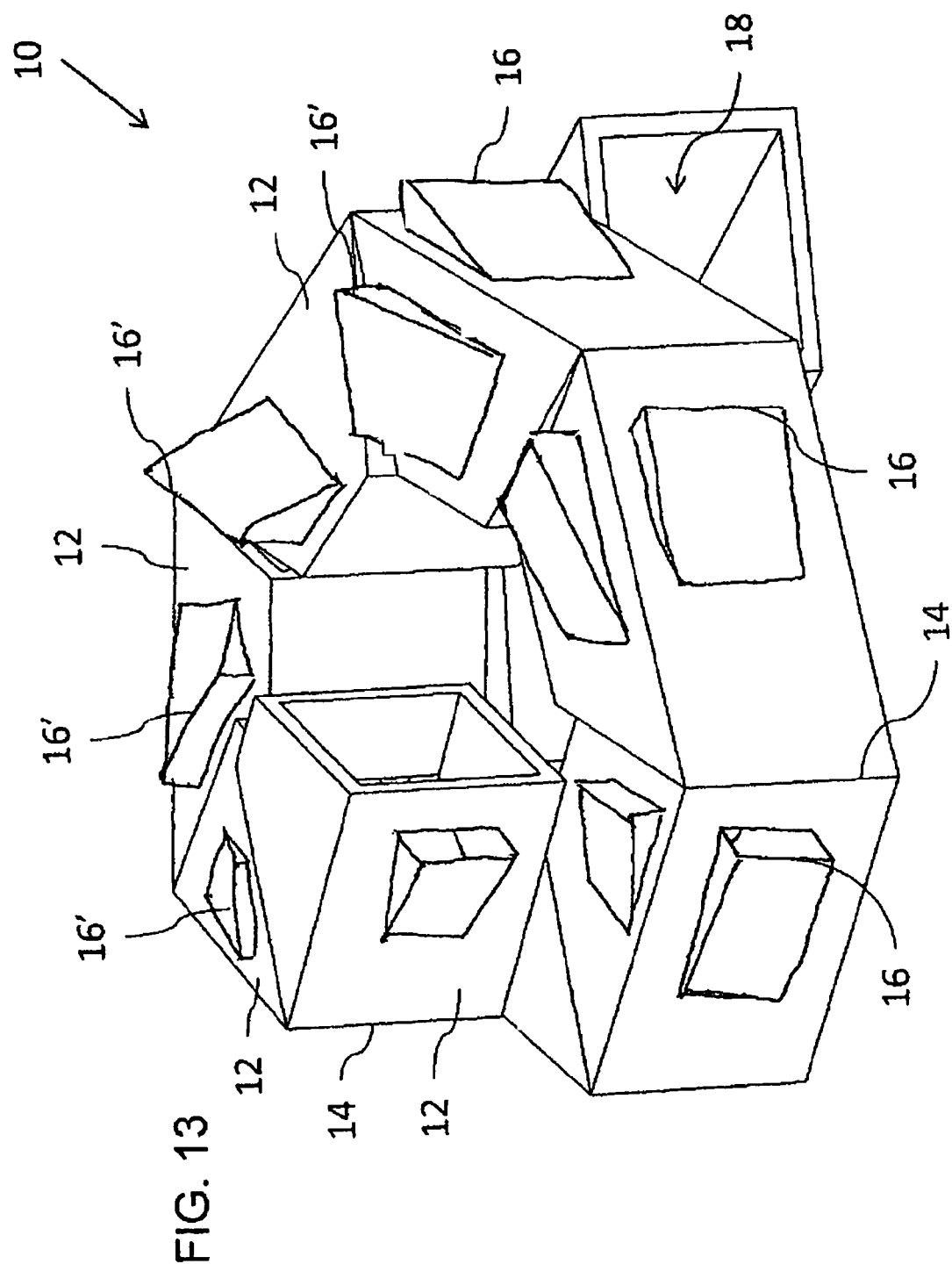
FIG. 13 is a schematic isometric view of a device, constructed and operative according to a further embodiment of the present invention, for removing material from within a body, the device being shown in a curved deployed state.

Finally, referring briefly to FIG. 13, it should be noted that the material-removing configurations of the present invention are not limited to spiral and helical configurations. For example, as illustrated in FIG. 13, elongated element 10 may be configured to progressively assume a conical deployed form as shown. This form allows cutting expansion in both radial and axial directions simultaneously.

It will be appreciated that the above descriptions are intended only to serve as examples, and that many other embodiments are possible within the scope of the present invention as defined in the appended claims.

What is claimed is:

1. A device for insertion into a body via an opening, and for removing material from within the body, the device comprising:
   an elongated element formed primarily from a plurality of hollow segments sequentially interconnected so as to form an effective hinge between adjacent of the segments, the segments and the effective hinges being configured such that:
   (a) the elongated element assumes an insertion configuration for insertion of the segments sequentially through an opening of a first dimension into the body; and
   (b) a portion of the elongated element inserted into the body progressively assumes a material removing configuration in which a relative position of each segment relative to an adjacent segment is delineated by the effective hinge together with abutment surfaces of sequentially adjacent segments in contact with each other, thereby defining a fully deflected state of the effective hinge, said material removing configuration having at least two dimensions exceeding said first dimension,
   wherein each of at least two of the segments is formed with at least one cutting configuration deployed so as to collect material into a hollow volume of the segments during progressive formation of said material removing configuration as the elongated element is advanced.

2. The device of claim 1, wherein the elongated element is substantially straightened when in said insertion configuration.

3. The device of claim 1, wherein the elongated element is resiliently biased to assume said material removing configuration.

4. The device of claim 1, wherein said material removing configuration is configured such that, as the elongated element is advanced, said material removing configuration progressively expands in at least two dimensions.

5. The device of claim 1, wherein said material removing configuration is configured to substantially close on itself so as to define a substantially contiguous contained volume.

6. The device of claim 1, wherein at least part of the elongated element assumes a spiral configuration in said material removing configuration.

7. The device of claim 1, wherein at least part of the elongated element assumes a helical configuration in said material removing configuration.

8. The device of claim 1, wherein at least part of the elongated element assumes a conical shape in said material removing configuration.

9. The device of claim 1, wherein said material removing configuration has three dimensions which all exceed said first dimension.

10. The device of claim 1, wherein each of said segments has a substantially rectangular cross-section.

11. The device of claim 1, wherein said at least one cutting configuration comprises at least one louver.

12. The device of claim 1, wherein said at least one cutting configuration comprises at least two cutting configurations deployed on at least two sides of one of said segments.

13. The device of claim 1, wherein said at least one cutting configuration comprises at least three cutting configurations deployed on at least three sides of one of said segments.

14. The device of claim 1, wherein said elongated element includes at least five of said hollow segments.

15. The device of claim 1, wherein said effective hinges between adjacent of the segments are implemented as integral hinges.

16. The device of claim 1, wherein said effective hinges between adjacent of the segments are implemented as hinge structures connecting separately formed segments.

17. The device of claim 1, wherein said effective hinges between adjacent of the segments are implemented as shape-memory hinges.

18. A method for removing material from a body, the method comprising:
   (a) providing a device comprising an elongated element formed primarily from a plurality of hollow segments sequentially interconnected so as to form an effective hinge between adjacent of the segments, the segments and the effective hinges being configured such that:
   (i) the elongated element assumes an insertion configuration for insertion of the segments sequentially through an opening of a first dimension into the body; and
   (ii) a portion of the elongated element inserted into the body progressively assumes a material removing configuration in which a relative position of each segment relative to an adjacent segment is delineated by the effective hinge together with abutment surfaces of sequentially adjacent segments in contact with each other, thereby defining a fully deflected state of the effective hinge, said material removing configuration having at least two dimensions exceeding said first dimension,
   wherein each of at least two of the segments is formed with at least one cutting configuration deployed so as to collect material into a hollow volume of the segments during progressive formation of said material removing configuration as the elongated element is advanced;

(b) deploying the device in a delivery system;

(c) forming an opening into the body;

(d) advancing the device through the opening into the body such that the device assumes the material removing configuration within the body; and (e) removing the device through the opening together with material collected within said hollow volume.

19. The method of claim 14, wherein said material is at least part of an intervertebral disc.

20. The method of claim 14, wherein said material is soft tissue.

21. The method of claim 14, wherein said material is hard tissue.

* * * * *